(12) United States Patent
Malinowski

(10) Patent No.: US 8,355,786 B2
(45) Date of Patent: Jan. 15, 2013

(54) LEAD CONNECTOR, LEAD ADAPTER, AND LEAD INSERTION APPARATUS

(75) Inventor: Zdzislaw B. Malinowski, Castaic, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 464 days.

(21) Appl. No.: 12/469,484

(22) Filed: May 20, 2009

(65) Prior Publication Data
US 2009/0228087 A1 Sep. 10, 2009

Related U.S. Application Data

(62) Division of application No. 10/741,412, filed on Dec. 19, 2003, now Pat. No. 7,539,542.

(60) Provisional application No. 60/439,168, filed on Jan. 9, 2003.

(51) Int. Cl.
*A61N 1/372* (2006.01)

(52) U.S. Cl. .......................................... 607/37; 607/116

(58) Field of Classification Search .............. 607/36–37, 607/116–120
See application file for complete search history.

(56) References Cited

U.S. PATENT DOCUMENTS

| | | |
|---|---|---|
| 4,142,532 A | 3/1979 | Ware |
| 4,180,078 A | 12/1979 | Anderson |
| 4,310,001 A | 1/1982 | Comben |
| 4,411,276 A | 10/1983 | Dickhudt et al. |
| 4,411,277 A | 10/1983 | Dickhudt |
| 4,461,194 A | 7/1984 | Moore |
| 4,516,820 A | 5/1985 | Kuzma |
| RE31,990 E | 9/1985 | Sluetz et al. |
| 4,540,236 A | 9/1985 | Peers-Trevarton |
| 4,603,696 A | 8/1986 | Cross, Jr. et al. |
| 4,614,395 A | 9/1986 | Peers-Trevarton |
| 4,712,557 A | 12/1987 | Harris |
| 4,715,380 A | 12/1987 | Harris |
| 4,840,580 A | 6/1989 | Saell et al. |
| 4,850,359 A | 7/1989 | Putz |
| 4,860,750 A | 8/1989 | Frey et al. |
| 4,869,255 A | 9/1989 | Putz |
| 5,070,605 A | 12/1991 | Daglow et al. |
| 5,082,453 A | 1/1992 | Stutz, Jr. |
| 5,086,773 A | 2/1992 | Ware |
| 5,241,957 A | 9/1993 | Camps et al. |
| 5,252,090 A | 10/1993 | Giurtino et al. |
| 5,261,395 A | 11/1993 | Oleen et al. |
| 5,324,312 A | 6/1994 | Stokes et al. |

(Continued)

OTHER PUBLICATIONS

U.S. Appl. No. 10/741,412 Official Communication mailed Nov. 26, 2007, 8 pages.

(Continued)

*Primary Examiner* — Joseph Stoklosa
(74) *Attorney, Agent, or Firm* — Frommer Lawrence & Haug LLP; Bruce E. Black

(57) ABSTRACT

A connector and adapter engage leads with each other or with an implantable medical device when a wedge is removed from the spring-loaded connector or adapter assembly, thereby permitting the connector or adapter to compress around the lead connector. The connector and adapter assembly may include a body with at least one lumen, at least one contact exposed within the at least one lumen of the body, at least one wire electrically connected to the at least one contact, at least one clamp ring capable of compressing around the body, and at least one wedge or similar tool capable of opening and closing the at least one clamp ring.

20 Claims, 6 Drawing Sheets

U.S. PATENT DOCUMENTS

| | | |
|---|---|---|
| 5,336,246 A | 8/1994 | Dantanarayana et al. |
| 5,354,326 A | 10/1994 | Comben et al. |
| 5,358,514 A | 10/1994 | Schulman et al. |
| 5,368,496 A | 11/1994 | Ranalletta et al. |
| 5,413,595 A | 5/1995 | Stutz, Jr. |
| 5,433,734 A | 7/1995 | Stokes et al. |
| 5,560,358 A | 10/1996 | Arnold et al. |
| 5,730,628 A | 3/1998 | Hawkins |
| 5,755,743 A | 5/1998 | Volz et al. |
| 5,766,042 A | 6/1998 | Ries et al. |
| 5,782,892 A | 7/1998 | Castle et al. |
| 5,800,495 A | 9/1998 | Machek et al. |
| 5,843,141 A | 12/1998 | Bischoff et al. |
| 5,906,634 A | 5/1999 | Flynn et al. |
| 5,951,595 A | 9/1999 | Moberg et al. |
| 5,968,082 A | 10/1999 | Heil et al. |
| 5,989,077 A | 11/1999 | Mast et al. |
| 6,006,135 A | 12/1999 | Kast et al. |
| 6,038,479 A | 3/2000 | Werner et al. |
| 6,038,481 A * | 3/2000 | Werner et al. ............ 607/119 |
| 6,112,120 A | 8/2000 | Correas et al. |
| 6,112,121 A | 8/2000 | Paul et al. |
| 6,154,678 A | 11/2000 | Lauro |
| 6,198,969 B1 | 3/2001 | Kuzma |
| 6,321,126 B1 | 11/2001 | Kuzma |
| 6,605,094 B1 | 8/2003 | Mann et al. |
| 6,609,029 B1 | 8/2003 | Mann et al. |
| 6,654,641 B1 | 11/2003 | Froberg |
| 6,741,892 B1 | 5/2004 | Meadows et al. |

OTHER PUBLICATIONS

U.S. Appl. No. 10/741,412 Official Communication mailed Sep. 2, 2008, 5 pages.

U.S. Appl. No. 10/741,412 Official Communication mailed Apr. 10, 2008, 7 pages.

* cited by examiner

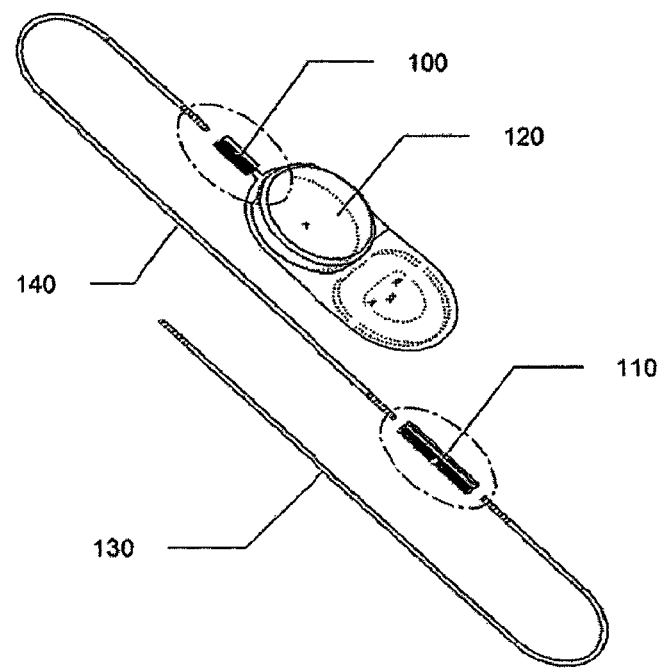
FIG. 1
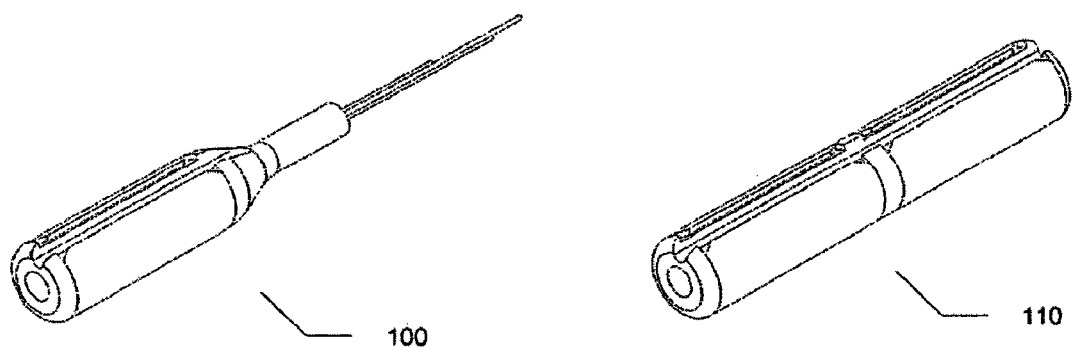
FIG. 2A
FIG. 2B

LEAD CONNECTOR, LEAD ADAPTER, AND LEAD INSERTION APPARATUS

This application is a divisional of U.S. patent application Ser. No. 10/741,412, filed Dec. 19, 2003, which claims the benefit of U.S. Provisional Patent Application Ser. No. 60/439,168, filed Jan. 9, 2003, both of which are incorporated herein by reference in their entirety.

FIELD OF THE INVENTION

The present invention relates to leads for use with implantable neurostimulation devices, and more particularly relates to connectors and adapters for connecting leads for use with implantable neurostimulation devices.

BACKGROUND OF THE INVENTION

The typical interconnection between an Implantable Pulse Generator (IPG) or other neurostimulation device and the stimulating and/or sensing lead takes up a considerable amount of volume in an IPG body. Because IPG bodies are implanted inside a patient's body, it is critical to minimize the size of the IPG. Hence, it is important to minimize the size of the typical interconnection between an IPG and a lead.

Further, many contemporary lead interconnections require additional tools to form a connection during surgery. The use of complicated additional tools during surgery increases the risk of human error during operation, complicates the operation by requiring additional steps to complete a procedure, and can add time to already time sensitive procedures.

Therefore, a need exists for a connector or adapter that forms a minimally-sized interconnection between leads and/or between a lead and an IPG that is located outside the IPG body and that requires no additional tools to complete the interconnection during operation.

SUMMARY OF THE INVENTION

The present invention addresses the above and other needs by providing a novel design of a minimally-sized connector and a minimally-sized adapter that connect leads to each other or to an IPG device (such as a spinal cord stimulator or a deep brain stimulator) and require no additional tools to form a stable electrical connection.

The design of the connector allows for coupling of a lead array with the implantable stimulation device outside the IPG device body, thereby minimizing the IPG size. The connector is firmly connected to the IPG device at the connector's proximal end, and the connector's distal end is used for connection with the lead or lead extension. The distal end of the connector includes a lumen in which a plurality of metal rings may be linearly arranged in a resilient body of the connector. The connection of the lead with the implantable device takes minimal space. The design of the adapter allows connection between multiple leads or lead extensions, even those from different manufacturers. The method of engaging a lead with the connector or the adapter is a very simple and quick procedure that does not require any additional tools such as a screwdriver or a hex wrench.

BRIEF DESCRIPTION OF THE DRAWINGS

The above and other aspects of the present invention will be more apparent from the following more particular description thereof, presented in conjunction with the following drawings wherein:

FIG. 1 is an isometric view of an IPG, a female connector, an extension lead, a female/female adapter, and a stimulation lead;

FIG. 2A is an isometric view of a female connector;

FIG. 2B is an isometric view of a female/female adapter;

Corresponding reference characters indicate corresponding components throughout the several views of the drawings.

DETAILED DESCRIPTION OF THE INVENTION

Figure 3:
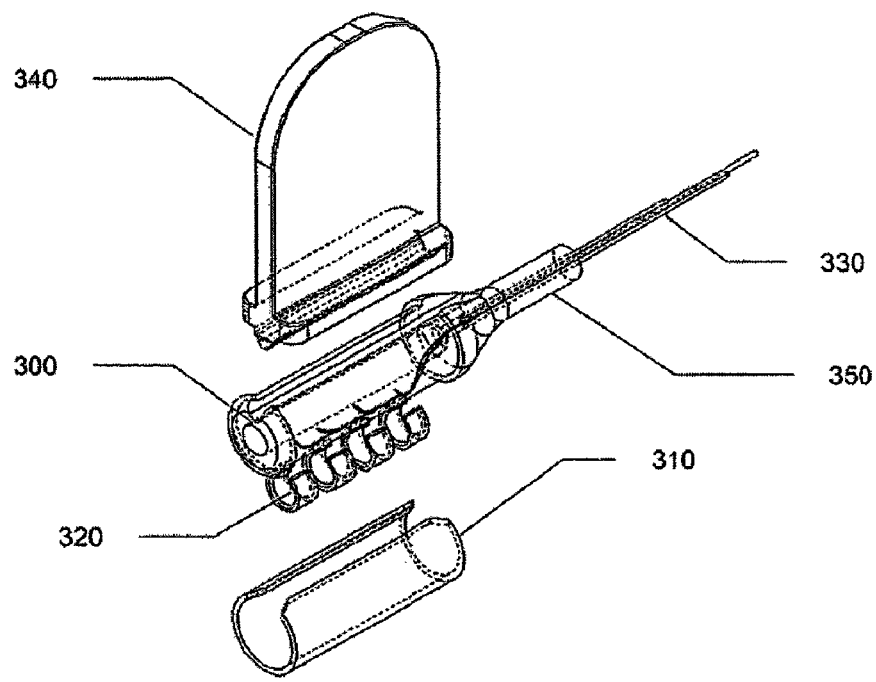
FIG. 3 is an exploded isometric view of the elements of a female connector assembly.

The following description is of the best mode presently contemplated for carrying out the invention. This description is not to be taken in a limiting sense, but is made merely for the purpose of describing the general principles of the invention. The scope of the invention should be determined with reference to the claims.

As shown in FIG. 1, a female connector 100 and female/female adapter 110 have been designed for use with an Implantable Pulse Generator (IPG) 120 or similar neurostimulation device. The invention relates to connection of those devices with stimulation leads 130 or extension leads 140. As used herein, "lead" may refer to a stimulation lead and/or sensing lead and/or extension lead (sometimes referred to as a lead extension) and/or a part of one or more of these. As shown in FIGS. 2A and 2B respectively, a female connector 100 and female/female adapter 110 are provided, each with a body including a lumen 510 (FIGS. 5A and 5B) in which one or more contacts 320 (see FIGS. 3, 4, and 6) are provided (e.g., two or more metal rings may be linearly arranged in the resilient body of female connector 100 or female/female adapter 110). While female connector 100 is capable of coupling one of a variety of different designs of a lead with the pulse generator or other neurostimulation device, female/female adapter 110 can be designed for simultaneously coupling two or more of the same or different lead constructions.

Figure 4:
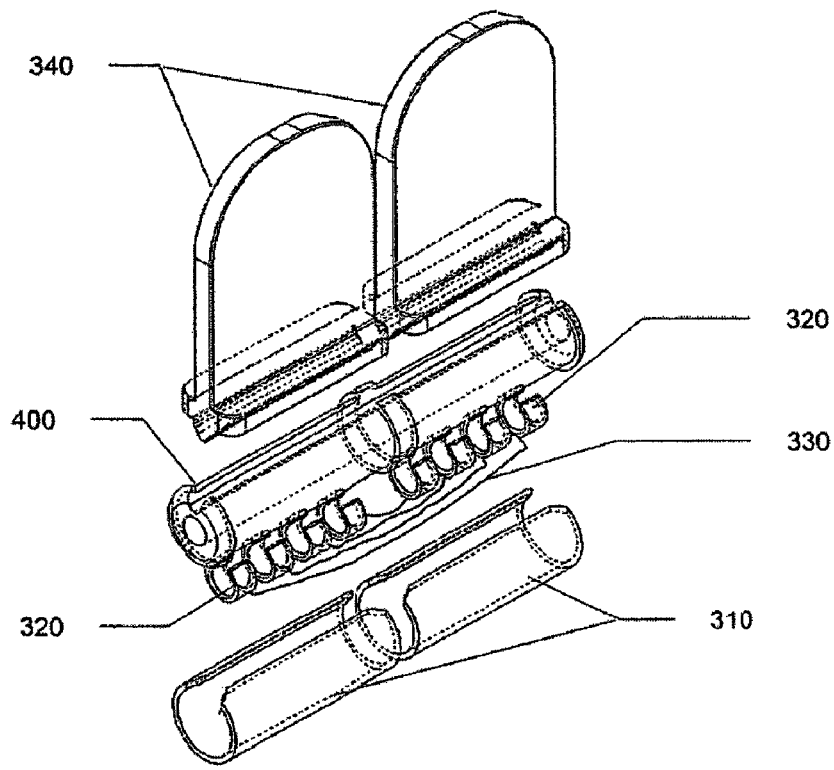
FIG. 4 is an exploded isometric view of the elements of a female/female adapter assembly.

As shown in FIGS. 3 and 4 respectively, the invention consists of five major components for the connector and adapter: connector body 300 or adapter body 400, clamp ring(s) 310, contacts 320 (e.g., metal rings), connecting wires 330, and wedge tool(s) 340 used for retaining female connector 100 or female/female adapter 110 in the "unlock" position. FIG. 3 shows the proximal end of connector body 300 attached to a lead 350. Wires 330 may electrically connect each of contacts 320 to corresponding contacts on the opposite end of a lead, to corresponding contacts 320 within the connector body 400 so that electrical connection may be established between the contacts and wires of two mating leads, to the electronic circuitry of an IPG, or to other structure to which electrical contact with contacts 320 is desired. At least one contact 320 is required for the present invention, however any number of contacts 320 may be used for the connector 100 or adapter 110 of the present invention.

Figure 5A:
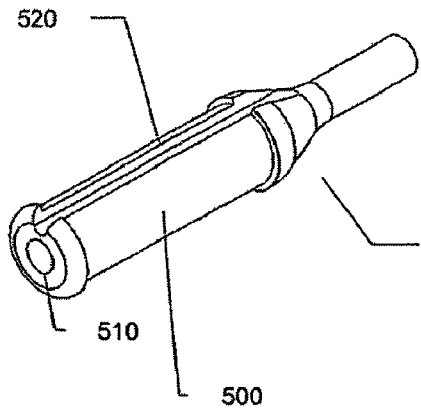
FIG. 5A is an isometric view of a female connector body.
Figure 5B:
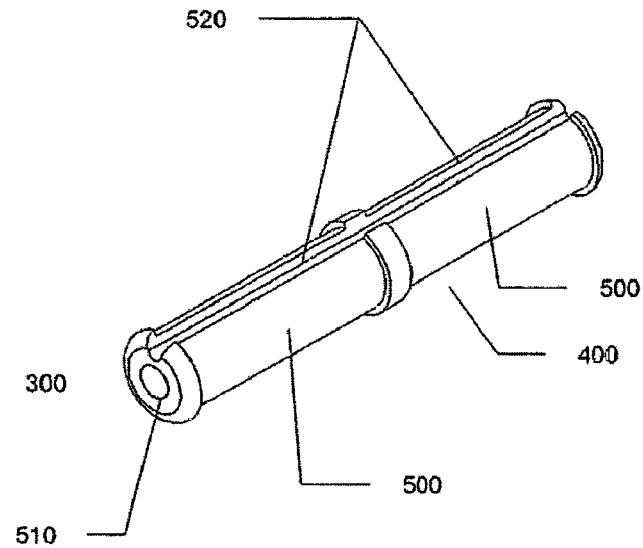
FIG. 5B is an isometric view of a female/female adapter body.

As shown in FIGS. 5A and 5B respectively, connector body 300 and adapter body 400 form the main part of female connector 100 (FIG. 2A) and female/female adapter 110 (FIG. 2B) and are typically made from a soft silastic material or other soft biocompatible material. Connector body 300 and adapter body 400 both preferably, but not necessarily, include at least one niche 500 for a clamp ring 310 (FIG. 7), a lumen 510, and a relief slit 520 along at least a portion of their lengths. Niche 500 nests clamp ring 310 (FIGS. 3 and 4) in the appropriate position along the length of connector body 300 or adapter body 400, resulting in a substantially continuous and flush exterior surface of clamp ring 310 with connector body 300 or adapter body 400, while preventing clamping ring 310 from sliding along the length of connector body 300 or adapter body 400. Lumen 510 serves as a receptacle for leads. Relief slit 520 provides space that is compressed by connector body 300 or adapter body 400 when female connector 100 or female/female adapter 110 is engaged with a lead, clamp ring(s) 310 are in place, and wedge tool(s) 340 are removed.

Figure 6:
FIG. 6 is an isometric view of a metal contact.

As shown in FIG. 6, contacts 320, such as metal rings, may be made from platinum, platinum/iridium or other low resistance biocompatible metal or alloy. Contacts 320 may be spaced within connector body 300 or adapter body 400 to line up with the contacts of the lead when the lead is inserted. Contacts 320 as shown in the example of FIG. 6 are formed of a split, tubular body.

Figure 7:
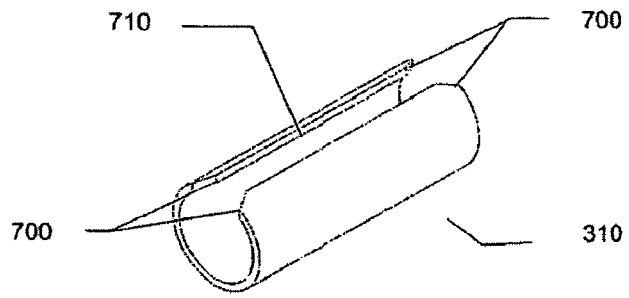
FIG. 7 is an isometric view of a clamp ring.

As shown in FIG. 7, clamp ring 310 is made from a biocompatible material such as a hard metal or polymer, for example, titanium, a titanium alloy (i.e., Ti 6/4), stainless steel, polyetheretherketone, or other material capable of achieving the purpose of clamp ring 310. The purpose of the clamp ring 310 is to act as a spring, which compresses contacts 320 (FIGS. 6, 3, and 4) against the contacts of the inserted lead. Connector body 300 and adapter body 400 are, e.g., silastic tubes that insulate clamp ring 310 from contacts 320. Clamp ring 310 in the example shown is a tubular body (while other suitable shapes are possible and fall within the scope of the invention), preferably with notches 700 on either end of a slit 710.

Notches 700, or other similar means, provide an entrance for wedge 340 to re-open clamp ring 310, thereby permitting leads, female connector 100 and female/female adapter 110 to be removable, reusable, and replaceable. Clamp ring 310 may be re-opened by aligning wedge end 800 (FIG. 8) with notches 700 and manually sliding wedge 340 in a direction parallel with slit 710 until wedge 340 has fully opened slit 710. During this process, a surgeon may use her or his hands to secure connector 100 or adapter 110 and provide counter-pressure to the force of wedge 340 while it is being inserted. Alternately, a surgeon may use any compatible tool, such as a pair of plyers with modified tips that resemble wedge end 800 and are capable of dividing slit 710 in a similar manner as wedge 340 but at both ends of connector 100 or adapter 110 simultaneously. Thus, the plyers or other tools would provide needed counter-pressure on clamp ring 310 so as to alleviate the need for a surgeon to manually provide such counter pressure. It is advantageous to be able to re-open clamp ring 310 for a patient who, for example, five years after an original surgery, must receive a new IPG to replace the original IPG in the patient's body. The IPG can be easily replaced without disturbing the positioning of its associated stimulation or sensing lead simply by detaching the IPG's associated connector or adapter by sliding wedge 340 between notches 700 thereby opening female connector 100 or female/female adapter 110, removing the original IPG, inserting the new IPG, and closing female connector 100 or female/female adapter 110 by removing wedge 340.

Figure 8:
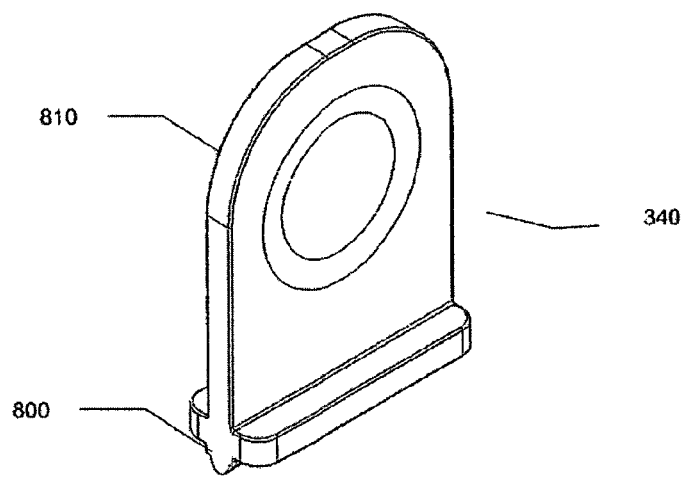
FIG. 8 is an isometric view of a wedge tool or insertion apparatus.

As shown in FIG. 8, wedge 340 is made from a titanium, hard polymer, or other biocompatible material and its function is to retain clamp ring 310 in the "unlocked" position with a wedge end 800 until a lead is inserted into female connector 100 or female/female adapter 110. A surgeon removes wedge end 800 from slit 710 (FIG. 7) by holding a handle 810 and pulling wedge 340 from slit 710 in a direction perpendicular to slit 710 or sliding wedge 340 out of slit 710 in a direction parallel with slit 710. The surgeon may use her or his fingers or any other helpful tool, such as a pair of plyers, to secure connector 100 or adapter 110 while wedge 340 is removed from slit 710.

Figure 9A:
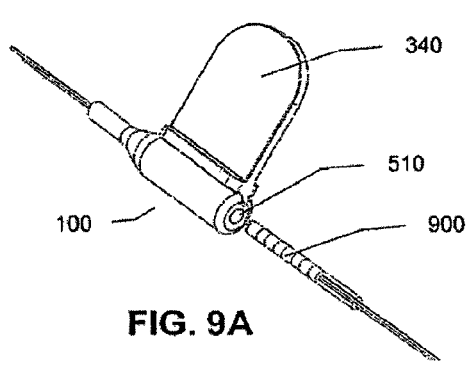
FIG. 9A is an isometric view of a female connector assembly and a lead.
Figure 9B:
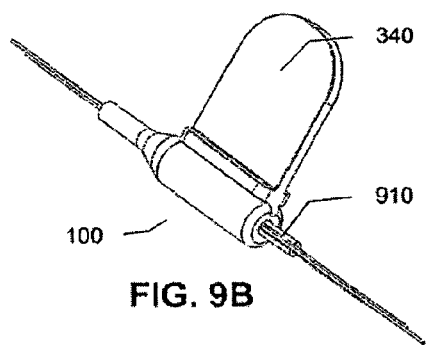
FIG. 9B is an isometric view of a lead inserted into the lumen of a female connector assembly.
Figure 9C:
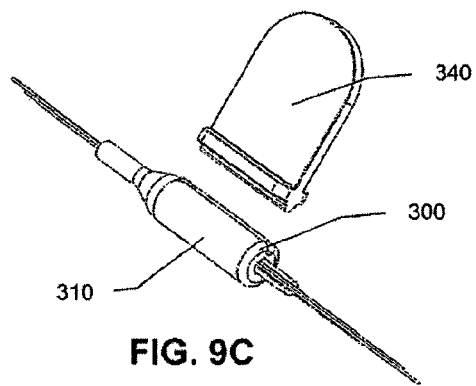
FIG. 9C is an isometric view of a female connector engaged with a lead and a wedge tool of the present invention removed.
Figure 9D:
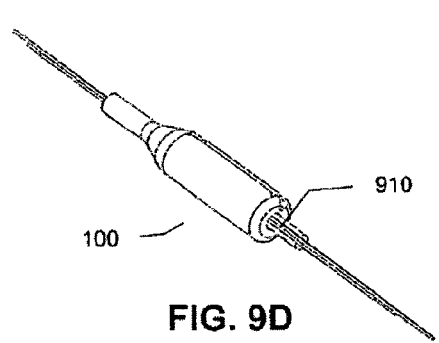
FIG. 9D is an isometric view of a female connector electrically and mechanically engaged with a lead.
Figure 10A:
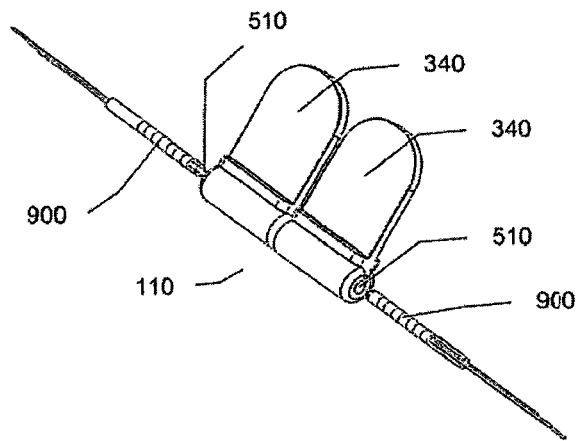
FIG. 10A is an isometric view of a female/female adapter assembly and two leads.
Figure 10B:
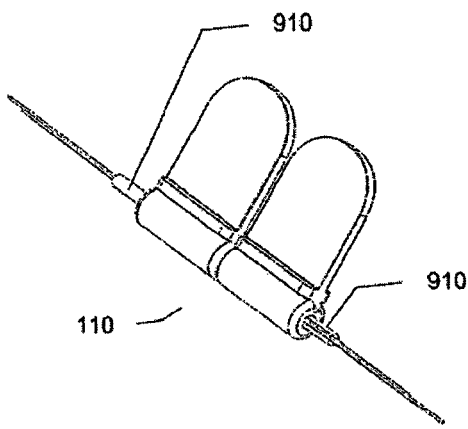
FIG. 10B is an isometric view of two leads inserted into the lumen of a female/female adapter assembly.
Figure 10C:
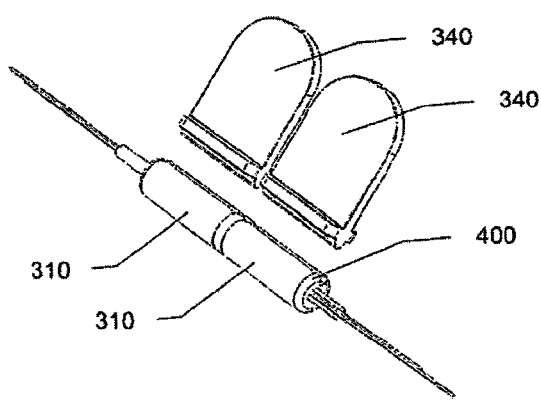
FIG. 10C is an isometric view of a female/female adapter engaged with two leads and two wedge tools of the present invention removed.
Figure 10D:
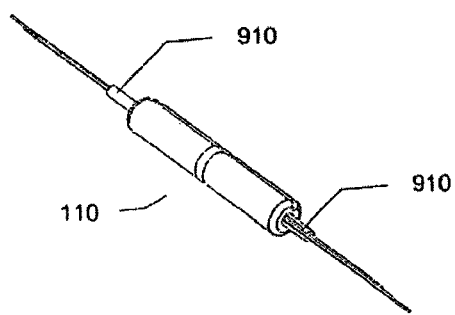
FIG. 10D is an isometric view of a female/female adapter electrically and mechanically engaging two leads.

As shown in the example of FIGS. 9A-9D, a lead connector 900 is engaged with female connector 100 through several simple steps and does not need the use of any sophisticated or additional tools. FIG. 9A shows a female connector 100 assembly ready for lead connector 900 insertion. FIG. 9B shows a lead 910 inserted into female connector 100. To ease lead connector 900 into connector lumen 510 (FIG. 9A), distilled water or other suitable substance can be used as a lubricant. FIG. 9C shows wedge 340 detached from compressed clamp ring 310. Removing wedge 340 releases the compressive energy of clamp ring 310 against connector body 300 and causes the female connector 100 assembly to lock around the lead connector 900. This action ensures the electrical connection between the contact surface(s) of the lead connector 900 and the contact(s) 320 (FIGS. 3 and 4) within the connector or adapter. The compressed body 300 of the connector presses the lead connector 900 with sufficient strength to prevent it from pulling out of female connector 100. FIG. 9D shows lead 910 electrically and mechanically engaged with female connector 100.

A similar exemplary method of engagement of FIGS. 9A-9D is shown in FIGS. 10A-10D for a female/female adapter 110, adapter body 400, two wedges 340, two leads 910, and two lead connectors 900. As explained above, female/female adapter 110 may accommodate two similar or dissimilar lead 910 designs.

To successfully insert and engage a lead with female connector 100 and/or female/female adapter 110, a lead insertion apparatus is used—described above as wedge tool 340. Wedge tool 340 is preferably, but not necessarily, factory-placed into slit 710 (FIG. 7) of clamp ring 310. With wedge tool 340 in slit 710, connector body 300 or adapter body 400 can be easily slid, perhaps with the use of lubricant such as distilled water, into place in the lumen of clamp ring 310. Clamp ring 310 remains in the "open" position until a lead connector 900 is inserted and ready for engagement with female connector 100 or female/female adapter 110. Lead connector 900 is inserted so that the contacts of the lead connector 900 are aligned with their corresponding contacts 320 inside the body of the female connector 100 or female/female adapter 110.

Preferably, the respective lumen 510 of the female connector 100 or female/female adapter 110 contains structure adapted to stop the insertion of a particular lead connector 900 so that the contacts of the lead connector 900 and the contacts 320 are properly aligned when the lead connector 900 is fully inserted. The dimensions of the stopping structure in each lumen 510 may vary depending on the structure of the particular type of lead connector inserted and the orientation of the contact(s) on that lead connector. For example, the embodiment of the female/female adapter 110 shown in FIGS. 10A-10D may include silastic stopping structure in the center of lumen 510, thus dividing the lumen in half so that each lead connector 900 may be fully inserted until the end of the respective lead connector 900 is blocked by the silastic stopping structure. The appropriate amount of stopping structure used would force the contacts of a fully inserted lead connector 900 to be perfectly aligned with corresponding contacts 320 on the respective end of the female/female connector 110.

After lead connector 900 insertion, wedge 340 is detached from clamp ring 310 (as discussed previously with reference to FIGS. 7 and 8) and lead 910 becomes electrically engaged with female connector 100 or female/female adapter 110.

Figure 11:
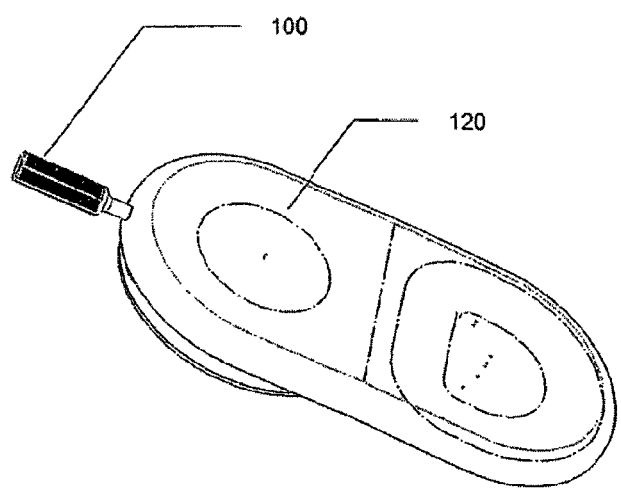
FIG. 11 is an isometric view of a female connector attached to an IPG.

FIG. 11 shows a female connector 100 attached to an IPG 120.

Figure 12:
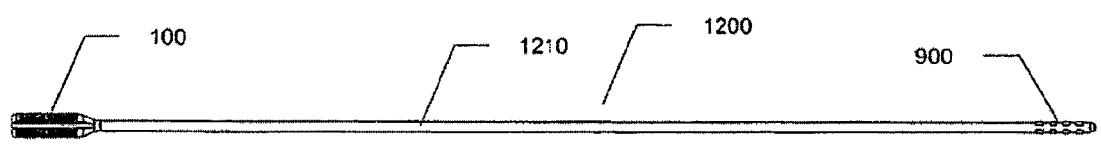
FIG. 12 is a side view of a lead extension with a female connector of the present invention.

FIG. 12 shows a lead extension 1200 which includes a female connector 100, a lead extension body 1210, and a lead connector 900.

Figure 13:
FIG. 13 is an isometric view of a female/male adapter of the present invention.

FIG. 13 shows a female/male adapter 1300, which includes a female connector 100 and a lead (or device) connector 900.

Figure 14:
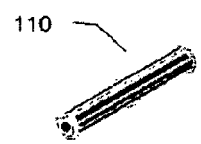
FIG. 14 is an isometric view of a female/female adapter.

FIG. 14 shows a female/female adapter 110. An alternate embodiment of an adapter, a male/male connector, is not shown but is considered part of the present invention. The male/male connector includes two lead connectors 900 at either end of the male/male connector. Further, as with all connectors and adapters of the present invention, female/female adapter 110 is capable of receiving any design of lead at either end of female/female adapter 110. Likewise, female/female adapter 110 can be modified to receive and connect to any number of leads or leads with multiple branches as, for example, in a "Y-shaped", "H-shaped", or "W-shaped" configuration. In these cases, multiple wires 330 (see FIG. 4) are attached and properly directed to and from contacts 320, some wires 330 of which may be split at an appropriate point along the pathway between contacts 320.

While the invention herein disclosed has been described by means of specific embodiments and applications thereof, numerous modifications and variations could be made thereto by those skilled in the art without departing from the scope of the invention set forth in the claims.

What is claimed is:

1. A lead connector for use with a medical device, comprising:
    a body defining at least one lumen extending from a proximal end of the body to a distal end of the body and enclosed axially by the body, the distal end of the body defining an opening into the lumen that is configured to receive and engage with a lead, and the proximal end of the body being configured for attachment to an Implantable Pulse Generator (IPG);
    at least one niche along an outside surface of the body;
    at least one contact along the at least one lumen of the body;
    at least one wire, electrically connected to the at least one contact; and
    at least one clamp ring nesting within the at least one niche, wherein the at least one clamp ring defines at least one slit along at least a portion of its length and is configured to compress into a closed position when an external tool is removed from the at least one slit, wherein in the closed position the clamp ring is configured and arranged to compress the body to prevent insertion of a lead into, or removal of a lead from, the body of the lead connector.

2. The connector of claim 1, further comprising at least one wedge.

3. The connector of claim 2, wherein the at least one clamp ring is opened when the at least one wedge is engaged with the at least one slit of the at least one clamp ring.

4. The connector of claim 2, wherein the at least one clamp ring is closed when the at least one wedge is removed from the at least one slit of the at least one clamp ring.

5. The connector of claim 1, wherein the at least one clamp ring defines at least one notch at at least one end of the at least one slit of the at least one clamp ring.

6. The connector of claim 1, further comprising at least one relief slit along at least a portion of the body.

7. The connector of claim 6, wherein the at least one relief slit extends along an entire length of the body.

8. The connector of claim 1, wherein the body is constructed of a soft biocompatible material and the clamp ring is constructed of a hard polymer.

9. The connector of claim 1, wherein the slit of the clamp ring extends along an entire length of the clamp ring.

10. The connector of claim 1, wherein the clamp ring is configured and arranged to at least partially surround the body.

11. The connector of claim 2, wherein the clamp ring is configured to assume an opened position when the wedge is engaged with the slit of the clamp ring, wherein the lead is configured to be removed from the lumen of the body when the clamp ring is in the opened position.

12. The connector of claim 1, wherein the clamp ring is configured to compress the at least one contact along the lumen of the body against at least one contact of the lead when the clamp ring is in the closed position.

13. A stimulation system comprising the connector of claim 1, an implantable pulse generator, and a lead coupled to the implantable pulse generator via the lead connector.

14. A lead connector comprising:
    a body defining at least one lumen extending from a proximal end of the body to a distal end of the body and enclosed axially by the body, the distal end of the body defining an opening into the lumen that is configured to receive and engage with a lead, and the proximal end of the body being configured for attachment to an Implantable Pulse Generator (IPG);
    a clamp ring having a slit along at least a partial length thereof, wherein the clamp ring is configured to at least partially surround the body; and
    a wedge configured to removably fit within the slit of the clamp ring;
    wherein the clamp ring is configured to compress into a closed position when the wedge is removed from the at least one slit, wherein in the closed position the clamp ring is configured and arranged to compress the body to prevent insertion of a lead into, or removal of a lead from, the body of the lead connector.

15. The connector of claim 14, wherein the clamp ring is configured to assume an opened position when the wedge is engaged with the slit of the clamp ring, wherein the lead is configured to be removed from the lumen of the body when the clamp ring is in the opened position.

16. The connector of claim 14, further comprising at least one electrical contact disposed within the lumen of the body.

17. The connector of claim 16, wherein the at least one electrical contact is configured to be compressed against a corresponding electrical contact disposed on the lead when the clamp ring is in the closed position.

18. The connector of claim 14, further comprising a relief slit along at least a portion of the body.

19. The connector of claim 14, wherein the slit of the clamp ring extends along an entire length of the clamp ring.

20. A stimulation system comprising the connector of claim 14, an implantable pulse generator, and a lead coupled to the implantable pulse generator via the connector.

* * * * *